United States Patent
Chow et al.

(10) Patent No.: US 9,259,439 B2
(45) Date of Patent: *Feb. 16, 2016

(54) DUAL-PHASE CEMENT PRECURSOR SYSTEMS FOR BONE REPAIR

(75) Inventors: Laurence C. Chow, Potomac, MD (US); Shozo Takagi, Gaithersburg, MD (US)

(73) Assignee: ADA FOUNDATION, Chicago, IL (US)

( * ) Notice: Subject to any disclaimer, the term of this patent is extended or adjusted under 35 U.S.C. 154(b) by 768 days.

This patent is subject to a terminal disclaimer.

(21) Appl. No.: 11/550,586

(22) Filed: Oct. 18, 2006

(65) Prior Publication Data

US 2007/0092580 A1 Apr. 26, 2007

Related U.S. Application Data

(60) Provisional application No. 60/728,888, filed on Oct. 21, 2005, provisional application No. 60/728,838, filed on Oct. 21, 2005.

(51) Int. Cl.
| | | |
|---|---|---|
| A61K 33/42 | (2006.01) | |
| A61L 27/12 | (2006.01) | |
| A61L 27/42 | (2006.01) | |
| A61L 27/46 | (2006.01) | |
| A61L 27/54 | (2006.01) | |

(52) U.S. Cl.
CPC ............. *A61K 33/42* (2013.01); *A61L 27/12* (2013.01); *A61L 27/425* (2013.01); *A61L 27/427* (2013.01); *A61L 27/46* (2013.01); *A61L 27/54* (2013.01); *A61L 2300/252* (2013.01); *A61L 2300/60* (2013.01)

(58) Field of Classification Search
CPC ............ A61K 33/42; A61L 2300/252; A61L 2300/60; A61L 27/12; A61L 27/425; A61L 27/427; A61L 27/46; A61L 27/54
USPC .............. 424/601, 602, 57; 106/690, 691, 35; 606/76, 77, 86 R, 92; 423/308; 623/23.62
See application file for complete search history.

(56) References Cited

U.S. PATENT DOCUMENTS

| | | | |
|---|---|---|---|
| 3,620,778 A | 11/1971 | Morrell | |
| 4,182,829 A | 1/1980 | Walkowiak et al. | |
| 4,357,165 A | 11/1982 | Helferich et al. | |
| 4,542,172 A | 9/1985 | Jochum et al. | |
| 4,612,053 A * | 9/1986 | Brown et al. ................... | 106/35 |
| 4,664,857 A | 5/1987 | Nambu | |
| 4,902,649 A | 2/1990 | Kimura et al. | |
| 5,092,888 A | 3/1992 | Iwamoto et al. | |
| 5,180,426 A * | 1/1993 | Sumita ........................... | 106/35 |
| 5,238,491 A | 8/1993 | Sugihara et al. | |
| 5,306,337 A | 4/1994 | Winkel et al. | |
| 5,342,441 A | 8/1994 | Mandai et al. | |
| 5,415,547 A | 5/1995 | Torabinejad et al. | |
| 5,501,727 A * | 3/1996 | Wang et al. ..................... | 106/35 |
| 5,508,342 A | 4/1996 | Antonucci et al. | |
| 5,520,992 A | 5/1996 | Douglas et al. | |
| 5,527,836 A * | 6/1996 | Yamamuro et al. ............ | 523/116 |
| 5,769,638 A | 6/1998 | Torabinejad et al. | |
| 5,900,254 A | 5/1999 | Constantz | |
| 5,997,624 A | 12/1999 | Chow et al. | |
| 6,028,125 A | 2/2000 | Combe et al. | |
| 6,197,846 B1 | 3/2001 | Combe et al. | |
| 6,325,992 B1 | 12/2001 | Chow et al. | |
| 6,387,978 B2 | 5/2002 | Ronan et al. | |
| 6,472,454 B1 | 10/2002 | Qian | |
| 6,500,004 B2 | 12/2002 | Jensen et al. | |
| 6,521,246 B2 | 2/2003 | Sapieszko et al. | |
| 6,559,200 B1 | 5/2003 | Kamohara et al. | |
| 6,566,418 B2 | 5/2003 | Imai et al. | |
| 6,605,294 B2 | 8/2003 | Sawhney | |
| 6,652,875 B1 | 11/2003 | Bannister | |
| 6,787,584 B2 | 9/2004 | Jia et al. | |
| 6,793,725 B2 | 9/2004 | Chow et al. | |
| 6,818,018 B1 | 11/2004 | Sawhney | |
| 6,905,516 B1 | 6/2005 | Lemaitre et al. | |
| 7,407,542 B2 * | 8/2008 | Lemaitre et al. ................ | 106/35 |
| 8,557,038 B2 * | 10/2013 | Chow .................... A61L 24/001 | 106/35 |
| 2003/0167093 A1 * | 9/2003 | Xu et al. ...................... | 623/23.56 |

(Continued)

FOREIGN PATENT DOCUMENTS

| | | |
|---|---|---|
| DE | 10021605 | 11/2001 |
| EP | 0639366 | 2/1995 |

(Continued)

OTHER PUBLICATIONS

S. Takagi, I. C. Chow, S. Hirayama, A. Sugawara. Premixed calcium-phosphate cement pastes, J. Biomed. Mater. Res. B, 2003, 67, 689-696.*
U. Gbureck, S. Dembski, R. Thull, J. E. Barralet. Factors influencing calcium phosphate cement shelf-life, Biomater. 2005, 26, 3691-3697.*
Brown and Chow, A New Calcium Phosphate Water Setting Cement, pp. 352-379 in Brown, Cements Research Progress, American Ceramic Society, OH, 1986.
Ginebra et al., Setting Reaction and Hardening of an Apatitic Calcium Phosphate Cement, J. Dent. Res. 76:905-912, 1997.
Constantz et al., Histological, Chemical, and Crystallographic Analysis of Four Calcium Phosphate Cements in Different Rabbit Osseous Sites, J Biomed Mater. Res. [Appl. Biomater.] 43:451-461, 1998.
Miyamoto et al., Histological and Compositional Evaluations of Three Types of Calcium Phosphate Cements When Implanted in Subcutaneous Tissue Immediately After Mixing, J. Biomed. Mater. Res. [Appl. Biomater.] 48:36-42, 1999.
Lee et al., Alpha-BSM(R): A Biomimetic Bone Substitute and Drug Delivery Vehicle, Clin. Orthop Rel. Res. 367:396-405, 1999.

(Continued)

*Primary Examiner* — Carlos Barcena

(57) ABSTRACT

Disclosed are dual-phase cement precursor systems and related methods and kits. The cement precursor systems are composed of a first and second discrete phases, at least one of which is aqueous. When combined, the cement precursor phases form a cement that is suitable as a bone graft material for bone repair procedures. In preferred embodiments, the materials are highly biocompatible, osteoinductive, and bioresorbable. A number of different but not mutually exclusive cement chemistries may be employed in the cement precursor systems. For instance, hydrogel-forming polymer cements, carboxyl/calcium cements, or calcium phosphate cements may be employed.

21 Claims, No Drawings

(56) References Cited

U.S. PATENT DOCUMENTS

| | | | |
|---|---|---|---|
| 2003/0232895 A1 | 12/2003 | Omidian et al. | |
| 2004/0009205 A1 | 1/2004 | Sawhney | |
| 2004/0110863 A1 | 6/2004 | Zech et al. | |
| 2004/0244651 A1 | 12/2004 | Lemaitre et al. | |
| 2006/0198863 A1* | 9/2006 | DePaula | 424/422 |
| 2006/0213398 A1* | 9/2006 | Barralet et al. | 106/690 |

FOREIGN PATENT DOCUMENTS

| | | |
|---|---|---|
| EP | 1384704 | 1/2004 |
| JP | S58-208205 | 12/1983 |
| JP | H02-034172 | 2/1990 |
| JP | 2311406 | 12/1990 |
| JP | H02-311406 | 12/1990 |
| JP | 06287133 A | 11/1994 |
| JP | H08-511964 | 12/1996 |
| WO | WO 03041753 | 5/2003 |

OTHER PUBLICATIONS

Ishikawa et al., Reaction of Calcium Phosphate Cements with Different Amounts of Tetracalcium Phosphate and Dicalcium Phosphate Anhydrous, J. Biomed. Mater. Res. 46:504-510, 1999.

Matsuya et al., Effects of Mixing Ratio and Ph on the Reaction Between Ca4[PO4]2O and CaHPO4, J. Mater. Sci.: Mater. in Med. 11:305-311, 2000.

Takagi et al., Morphological and Phase Characterizations of Retrieved Calcium Phosphate Cement Implants, J. Biomed. Mater. Res. [Appl. Biomater.]58:36-41, 2001.

Shindo et al., Facial Skeletal Augmentation Using Hydroxyapatite Cement, Arch. Otolaryngol. Head Neck. Surg., 119:185-190, 1993).

Sugawara et al., In vitro Evaluation of the Sealing Ability of a Calcium Phosphate Cement When Used as a Root Canal Sealer-Filler, J. Endodont. 16:162-165, 1990).

Chohayeb et al., Evaluation of Calcium Phosphate as a Root Canal Sealer-Filler Material, J. Endodont. 13:384-387,1987.

Takagi et al., "Properties of premixed calcium phosphate cement pastes," J. Biomed Mater Res. [Applied Biomater] 67B:689-696 (2003).

Chow et al., "Rapid-Hardening, Pre-mixed Calcium phosphate cement pastes," Abs. No. 844, J. Dent. Res., Spec. Iss. A82 (2003).

Carey et al., "Premixed Rapid-Setting Calcium Phosphate Composites for Bone Repair," Biomaterials 24:5002-14 (2005).

Nauman C.H.J., Love R.M., Biocompatibility of Dental Materials Used in Contemporary Endodontic Therapy: A Review. Part 2 Root-Canal Filling Materials, Int. Endod. J. 36:147-160 (2003).

Frank, A., Therapy for the Divergent Pulpless Tooth by Continued Apical Formation, J. Am. Dent. Ass. 72:87-93 (1966).

Weisenseel J.A. et al., Calcium Hydroxide As an Apical Barrier, J. Endod. 13:1-5 (1987).

Schumacher J.W., Rutledge R.E., An Alternative to Apexification, J. Endod. 19:529-531 (1993).

Kratchman, S., Perforation Repair and One-Step Apexification Procedures, Dent. Clin. N. Am. 48 291-307 (2004).

Giuliani V. et al.: The Use of MTA in Teeth With Necrotic Pulps and Open Apices, Dent. Traumatol. 18(4):217-21 (2002).

Shabahang, S., Torabinejad, M., Treatment of Teeth With Open Apices Using Mineral Trioxide Aggregate, Pract. Periodont. Aesthe. Dent. 12(3):315-320 (2000).

PCT International Search Report dated Apr. 18, 2007.

Supplementary European Search Report of Application No. EP 06836421 dated Apr. 19, 2011.

Examiner's first report on Australian patent application No. 2006304803, dated Jul. 26, 2011, pp. 1-3.

USPTO Office Action mailed Mar. 13, 2012, U.S. Appl. No. 11/550,543.

Supplementary European Search Report of EP 06817258, dated May 5, 2011.

Japanese Office Action, Appln. No. 2008-536846, dated Jul. 3, 2012 (Translation of Notice of Reasons for Rejection is also attached).

Notice to File a Response (English translation of Korean Office Action) Application No. 10-2008-7012014 dated May 27, 2013, pp. 1-7.

Shimizu et al., Computer generated English translation of JP 06-287133A, Oct. 11, 1994, p. 1-5.

USPTO Office Action mailed May 7, 2013 U.S. Appl. No. 11/550,543.

USPTO Office Action mailed Oct. 24, 2013 U.S. Appl. No. 11/550,543.

* cited by examiner

DUAL-PHASE CEMENT PRECURSOR SYSTEMS FOR BONE REPAIR

CROSS REFERENCE TO RELATED APPLICATION

This application claims priority to prior U.S. Provisional Patent Applications 60/728,888 and 60/728,838, both filed on Oct. 21, 2005. The contents of these two provisional patent applications are incorporated by reference. In addition, this application incorporates by reference the entire content of U.S. patent application Ser. No. 11/550,543, filed on even date herewith, entitled "Dental and Endodontic Filling Materials and Methods," which in turn claims priority to U.S. Provisional Patent Application 60/728,838.

STATEMENT OF FEDERALLY SPONSORED RESEARCH

The invention was made in the course of research supported at least in part by Grant DE11789 from the National Institute of Dental and Craniofacial Research and carried out at the National Institute of Standards and Technology. The U.S. government may have certain rights to the invention.

TECHNICAL FIELD

Generally, the invention is in the field of cements that are useful in connection with bone repair procedures. Preferred embodiments of the invention provide dual-phase cement precursor systems in which the cement precursors take the form of first and second precursor phases. The phases initially are separate, but a cement suitable for bone repair procedures may be formed upon blending of the first and second phases.

BACKGROUND OF THE INVENTION

Several types of self-hardening calcium phosphate compositions have been studied (Brown and Chow, A New Calcium Phosphate Water Setting Cement, pp. 352-379 in Brown, *Cements Research Progress*, American Ceramic Society, Ohio, 1986; Ginebra et al., Setting Reaction and Hardening of an Apatitic Calcium Phosphate Cement, *J. Dent. Res.* 76:905-912, 1997; Constantz et al., Histological, Chemical, and Crystallographic Analysis of Four Calcium Phosphate Cements in Different Rabbit Osseous Sites, *J Biomed Mater. Res. [Appl. Biomater.]* 43:451-461, 1998; Miyamoto et al., Histological and Compositional Evaluations of Three Types of Calcium Phosphate Cements When Implanted in Subcutaneous Tissue Immediately After Mixing, *J. Biomed. Mater. Res. [Appl. Biomater.]* 48:36-42, 1999; Lee et al., Alpha-BSM(R): A Biomimetic Bone Substitute and Drug Delivery Vehicle, *Clin. Orthop Rel. Res.* 367:396-405, 1999. Because of its chemical and crystallographic similarity to the carbonated apatitic calcium phosphate mineral found in human bones and teeth, hydroxyapatite has been one of the most often used restorative materials for the repair of human hard tissues One of the calcium phosphate compositions, developed by Brown and Chow in 1986 and named calcium phosphate cement, or CPC, self-hardens to form hydroxyapatite as the primary product. The term "self-harden" refers to the paste being able to harden by itself. For example, the CPC paste can be placed into a bone cavity, and can self-harden after contact with an aqueous medium. CPC typically may be composed of particles of tetracalcium phosphate (TTCP: $Ca_4(PO_4)_2O$) and dicalcium phosphate anhydrous (DCPA: $CaHPO_4$) that react in an aqueous environment to form solid hydroxyapatite, Ishikawa et al., Reaction of Calcium Phosphate Cements with Different Amounts of Tetracalcium Phosphate and Dicalcium Phosphate Anhydrous, *J. Biomed. Mater. Res.* 46:504-510, 1999; Matsuya et al., Effects of Mixing Ratio and Ph on The Reaction Between $Ca_4[PO_4]_2O$ and $CaHPO_4$, *J. Mater. Sci.: Mater. in Med.* 11:305-311, 2000; Takagi et al., Morphological and Phase Characterizations of Retrieved Calcium Phosphate Cement Implants, *J. Biomed. Mater. Res. [Appl. Biomater.]* 58:36-41, 2001. Calcium phosphate compositions (such as CPC) are highly promising for a wide range of clinical uses due to their excellent biocompatibility, osteoconductivity and bone replacement capability. For example, CPC has been studied for use in the reconstruction of frontal sinus and augmentation of craniofacial skeletal defects (Shindo et al., Facial Skeletal Augmentation Using Hydroxyapatite Cement, *Arch. Otolaryngol. Head Neck. Surg.*, 119:185-190, 1993), endodontics (Sugawara et al., In vitro Evaluation of the Sealing Ability of a Calcium Phosphate Cement When Used as a Root Canal Sealer-Filler, *J. Endodont.* 16:162-165, 1990), and root canal applications (Chohayeb et al., Evaluation of Calcium Phosphate as a Root Canal Sealer-Filler Material, *J. Endodont.* 13:384-387, 1987).

Most of the presently available calcium phosphate cements are mixed with an aqueous solution prior to use. Accordingly, the ability of the surgeon to properly mix the cement and then place the cement paste into a bone defect within the prescribed time prior to cement hardening is a crucial factor in achieving optimum results. The art thus has recognized the desirability of providing pre-mixed cement pastes that are stable as provided but that harden only after being introduced to the bone defect and positioned appropriately. Pre-mixed self-hardening cements may be formulated by combining glycerol, sodium phosphate, hydroxypropyl methyl cellulose and calcium phosphate cement powders, as described in Takagi et al., "Properties of premixed calcium phosphate cement pastes," *J. Biomed Mater Res. [Applied Biomater]* 67B:689-696 (2003). The hydroxypropyl methyl cellulose and sodium phosphate used in such pastes are believed to improve paste cohesiveness and accelerate cement hardening, respectively. The hardening times of the forgoing cements are about 60 minutes, which is much longer then 5- to 30-minute setting time desired in many cases.

Organic acids, such as glycolic, citric, tartaric, malonic, malic, maleic, and so forth, may be used as setting accelerators instead of sodium phosphate. In such cases, the pre-mixed cements can harden in significantly shorter times (10 minutes to 35 minutes) (Chow et al., "Rapid-Hardening, Pre-mixed Calcium phosphate cement pastes," Abs. No. 844, *J. Dent. Res.*, Spec. Iss. A82 (2003)). The rapid hardening of these pre-mixed pastes is due to formation of carboxyl/calcium complexes, rather than the formulation of hydroxyapatite, which is the mechanism responsible for cement hardening in most conventional calcium phosphate cements. Despite the lack of hydroxyapatite formulation, several carboxylic acid/calcium phosphate cements had been reported to produce excellent bone defect repair results in vivo.

A third type of pre-mixed calcium phosphate cement has been reported (Carey et al., "Premixed Rapid-Setting Calcium Phosphate Composites for Bone Repair," Biomaterials 24:5002-14 (2005)). The cement hardening in these pre-mixed cements results from formulation of a hard hydrogel produced by a reaction between chitosan, a water soluble polymer, and an alkaline compound such as tetracalcium phosphate or calcium hydroxide. After initial hardening, further reactions between calcium phosphate salts form hydroxyapatite as a major end product in the cement.

To provide stability, the heretofore described cements are formulated as non-aqueous pre-mixed materials. Cement hardening does not begin until these precursors are placed into a bone defect, whereupon water from surrounding tissues enters into the cement. These cements, while often possessing excellent physical properties, sometimes can be limited in utility. Cement hardening in the interior of the cement mass may be slow under some clinical bone grafting conditions, for instance, wherein the amount of water available from the tissues is limited, or wherein the interior of the cement is more than several millimeters away from the nearest graft-tissue interface. Additionally, such cements typically are required to be formulated to be able to react extremely rapidly when exposed to moisture. Such formulations typically do not have a long shelf life, in light of the difficulties inherent in excluding moisture during manufacture and storage.

SUMMARY OF THE INVENTION

Generally, the invention provides, in preferred embodiments, a dual-phase cement precursor system that comprises first and second separate phases. The phases themselves are not cements, but they may be combined to form a biocompatible cement that is useful in connection with bone repair procedures. In preferred embodiments, the cements thus formed are highly biocompatible, osteoconductive, and bioresorbable. A number of different but related and non-mutually exclusive cement chemistries may be employed in connection with the invention. For instance, in preferred embodiments, the cement may be a carboxyl/calcium cement, a hydrogel-forming polymer cement, or a calcium phosphate cement. At least one of the two phases is aqueous, to allow the cement to set without the need to uptake water from surrounding tissue.

Also encompassed by the invention are various kits and methods. In a preferred embodiment, a kit comprises the heretofore described cement precursor system, in one of its various embodiments, and a dispensing device. The invention also encompasses in some embodiments a method for bone repair, the method comprising providing a cement precursor system and applying a blend of the first and second precursor phases to an area where bone repair is desired.

Further attributes of the preferred embodiments of the invention are described hereinbelow.

DETAILED DESCRIPTION OF THE PREFERRED EMBODIMENTS

The cements that may be prepared from the cement precursors in accordance with the present invention are useful in connection with bone repair, by which is contemplated any bone grafting or other procedure used to correct defective or incorrectly formed bones, damages bones, and the like. The bone repair procedure may be performed in any animal, such as a human.

It is contemplated that a cement is a material that will set up, or harden, over a period of ninety minutes or less, when the cement is used at room temperature (20-25° C.). Cement precursors are materials that in ordinary use themselves are not cements, but that may be blended with another precursor to form a cement. The cement precursors are provided in the form of a dual-phase cement precursor system, by which is contemplated a system that includes at least two (but optionally additional) precursor phases. Each of the phases comprises a compound or composition, and each phase in the dual-phase system is different from at least one other phase in the system. The phases themselves are not cements, in that the phases themselves do not set to form a hard material in ordinary use. Rather, when the phases are combined, a cement is formed thereby.

The system generally includes the two phases, which may be provided together in a container that is equipped to keep the phases separate until use. Any suitable container may be used in conjunction with the invention, and thus, for instance, the container may be any appropriate box, or bag, or package. In some cases, the container may be an appropriately configured syringe. The container may contain separate vials for the precursor phases, or separate compartments for the phases.

Preferably, the system is provided in the form of a kit, the kit including the dual phase cement precursor system and an appropriate mixing device. The mixing device may be conventional, or may otherwise be a device suitable for use in conjunction with the cement precursor systems taught. The prior art has provided a microdispenser with a static mixing tip, the mixing tip comprising an auger-like structure that allows the two phases to be blended rapidly and subsequently to be applied to the desired area. An example of such a device is the Dual-barrel 9 mL Micro Dispensing System by Tah Industries, Robinsville, N.J. The invention contemplates the use of this device, or an analogous device that is specifically designed for medical usage. In some embodiments, the microdispensers may include a region that serves as the container for the phases, by providing separate holding chambers for the first and second phases.

Each phase preferably is sufficiently stable to permit transport and reasonable storage prior to use. Stability may be measured by any technique or using any criteria deemed appropriate. In accordance with one such technique, a sample of the material or materials constituting the phase is heated to a temperature of 50° C., and held at this temperature for seven days. The material then is used in the formation of a cement, and the setting time of the cement is evaluated as compared with the original setting time of a similar cement made without thermal treatment of either of the phases. If the setting time of the cement made with the thermally treated phase is approximately equal to the setting time of the similar cement, the phase may be deemed suitably stable for use in conjunction with the present invention. The invention is not limited to cement precursor systems that meet this criterion; rather, the foregoing is provided to illustrate one of but many possible methods for evaluating stability.

The phases themselves may be in any suitable form, so long as at least one of the phase is aqueous. The water present in the aqueous phase generally should be present as liquid water, although it is contemplated in some embodiments that water may be present solely in the form of hydrates of solid materials. The other phase may be an aqueous phase, if an aqueous phase would be suitably stable for the other materials in the phase. Alternatively, the other phase may be a non-aqueous or substantially non-aqueous solid phase, or may be a liquid non-aqueous or substantially non-aqueous phase. By "substantially non-aqueous is contemplated that essentially no hydrated or liquid water is present in the phase. It is contemplated that in a substantially non-aqueous phase there will be trace amounts of moisture present, such as moisture that is unavoidably present notwithstanding reasonably prudent steps to exclude such moisture. In some embodiments, a liquid non-aqueous phase is provided. The liquid can be any suitable room temperature liquid, examples of which include glycerin, glycerol, ethanol, propanol, certain polyethylene glycols, and propylene glycol. Glycerin is deemed particularly preferred, in light of its biocompatibility and complete miscibility with water.

In forming a cement, the phases may be blended in any suitable amounts. When each phase is a liquid, preferably the phases are formulated such that the volumetric ratio of mixing ranges from 0.1-10, more preferably, 0.25-4.

The cement precursors may be any material suitable for use in forming a biocompatible cement, the term "biocompatible" (when used in conjunction with a cement) contemplating a cement that is not rejected by soft tissue or hard tissue when used in vivo in the intended application. Numerous cement chemistries may be used in conjunction with the convention. In a first preferred embodiment, a calcium phosphate cement is employed. Calcium phosphate cements are deemed to be those cements in which at least two dissimilar calcium phosphate materials are present respectively in the two precursor phases, and in which, upon blending, a complex or mixture or third calcium phosphate material (hydroxyapatite, for instance) is formed. In such cements, some of the third material may be present in one or both of the precursor phases. In a second preferred embodiment, a carboxyl/calcium cement is employed. In such cements, one of the phases includes a carboxylic acid or carboxylate, and the other phase includes a calcium compound, and in which, upon blending of the phases, a carboxyl/calcium complex is formed. Additional materials may be present; for instance, the first phase may include a calcium compound in addition to the carboxylic acid or carboxylate, so long as the phase is stable and does not form a hardened cement in ordinary use prior to blending with the second phase. For instance, the first phase may include a calcium phosphate compound that is sufficiently acidic that it does not dissociate and thus does not react with the carboxylic acid or carboxylate, even in the presence of any water present in this phase. In a third preferred embodiment, a hydrogel cement is employed. A hydrogel cement is deemed to be a cement in which a hydrogel-forming polymer and a hydrogel former are present in at least one of the precursor phases. In many (but not all) embodiments, the hydrogel-forming polymer is present in one of the phases, and the hydrogel former is present in the other phase. Upon blending of the phases, a hardened hydrogel is formed. These cement chemistries are not mutually exclusive, and it is possible that two or more mechanisms of cement formation may be present in a given cement precursor system. Likewise, other cement chemistries may be employed instead of or in addition to the foregoing.

Where a carboxyl/calcium cement is employed, one of the phases contains a carboxylic acid or the salt of a carboxylic acid. Any suitable biocompatible carboxylic acid or salt may be used in conjunction with the invention, and accordingly the term "carboxyl" is deemed to include both the acid and the salt forms of organic acids. In preferred embodiments, the carboxylic acid or salt is at least one acid that is selected from among glycolic, citric, tartaric, glycerophosphoric, malonic, malic, and maleic acids. It is not necessary that the pH of the phase that includes the carboxylic acid or salt be in the acidic range. More generally, any other suitable acid may be used in conjunction with the invention.

In such systems, the other phase contains a calcium compound. Any suitable calcium compound may be used in conjunction with this embodiment of the invention. In preferred embodiments, the calcium compound is a calcium phosphate having a Ca/P ratio ranging from 0.5-2.0. Alternatively, or in addition thereto, the calcium compound may be a suitable calcium salt, or any suitable calcium compound that is sparing soluble in acid. Exemplary calcium compounds suitable for use in conjunction with the invention include tetracalcium phosphate (TTCP), dicalcium phosphate anhydrous (DCPA), dicalcium phosphate dihydrate (DCPD), monocalcium phosphate anhydrous (MCPA), monocalcium phosphate monohydrate (MCPM), alpha-tricalcium phosphate (alpha-TCP), beta tricalcium phosphate (beta-TCP), hydroxyapatite (HA), amorphous calcium phosphate (ACP), octacalcium phosphate (OCP), calcium deficient hydroxyapatite, carbonate-containing hydroxyapatite (CHA), fluoride-containing hydroxyapatite (FHA), calcium lactate, calcium sulfate, calcium gluconate, calcium lactate gluconate, calcium glycerophosphate, calcium silicate, calcium hydroxide, and other biocompatible calcium compounds with a solubility of at least about 2 wt. % in the acid environment. Generally, calcium compounds that are biocompatible and that form a suitable cement may be used. The selection of a particular calcium compound may be based on numerous factors, including for instance the reactivity of the compound with the selected acid, and also the overall acid and base contents of the cement, and the desired end cement products.

Generally, in each phase, the acid and calcium compound respectively may be present in any suitable amounts. The acid is preferably present in an aqueous phase in an amount ranging from about or exactly 1 to about or exactly 75 percent by weight of the total phase, more preferably, about or exactly 5 to about or exactly 35 percent. The calcium compound may or may not be present in an aqueous phase. Further details concerning the preferred ranges of calcium may be found in the examples set forth herein below.

When the calcium and carboxyl phases are combined, a cement is formed. The cement is formed by calcium in combination with a dissociated carboxylic acid residue ($RCOO^-$). In some embodiments, calcium may be present in the carboxyl phase of the cement, so long as the cement is stable (for instance, at sufficiently low pH). In such embodiments, some of the calcium from the carboxyl phase may contribute to the formation of the carboxyl/calcium setting cement. In such embodiments, the calcium-containing phase may contribute to cement formation in part by causing a rise in pH. Generally, in these embodiments, the pH of the cement should range from about 2-9 prior to setting.

In the case of hydrogel cements, the phases collectively include a hydrogel-forming polymer and the hydrogel former. In some embodiments, one of the phases includes a hydrogel-forming polymer and the other phase includes the hydrogel former. In other embodiments, the polymer and former initially are present together in one phase, that phase being at least substantially non-aqueous. In these embodiments, the other phase is an aqueous phase. The hydrogel-forming polymer may be any suitable polymer that is biocompatible and that will form a hardened hydrogel upon contact with the hydrogel former. Particularly preferred hydrogel-forming polymers include chitosan and biocompatible chitosan derivatives, alginic acid and alginic acid derivatives, in particular alginates, and pectinic acid and pectinic acid derivatives, in particular pectinates. Suitable alginic acid derivatives include sodium alginate, propylene glycol alginate, and other soluble alginate salts. Suitable pectinic acid derivatives include sodium pectinate and other suitable pectinate salts.

When the polymer is chitosan, the polymer will form a hydrogel upon exposure to alkalinity. Accordingly, any suitable alkaline agent, such as sodium hydroxide, potassium hydroxide, or calcium hydroxide, and calcium, sodium, or potassium salts of phosphoric acid or silicic acid, may be used as the hydrogel former. However, calcium-containing materials, in particular, calcium hydroxide, calcium phosphate, and calcium silicate, are preferred in bone cement applications. When the hydrogel-forming polymer includes alginic or pectinic acid or a derivative thereof, hydrogel formation occurs via formation of complexes with calcium, and thus the hydrogel former should be a material that includes calcium. Particularly preferred materials include the calcium compounds referenced hereinabove, such as TTCP, DCPA, and the like. Other suitable calcium compounds include calcium oxide, calcium chloride, calcium lactate, calcium glutonate, calcium silicate, and calcium carbonate. Again, as described hereinabove, the polymer and hydrogel former may be present in the precursor phases in any suitable amounts. Generally, each material may be present in amounts of from about or exactly 1 to about or exactly 75 percent by weight of the total phase, more preferably, about or exactly 5 to about or exactly 35 percent by weight of the total phase.

The cement alternatively may comprise a calcium phosphate cement. In such cements, a calcium phosphate precursor is present in one of the phases, and a dissimilar calcium phosphate precursor is present in the other one of the phases. When blended, a calcium phosphate complex, or third calcium phosphate, solidifies to form the cement. In many cases, hydroxyapatite or DCPD is formed. The phases need not include only a single calcium phosphate material, and thus, for instance, the phases each may include multiple calcium phosphate materials, and some of the third calcium phosphate material may be present initially in either or both of the phases.

Any suitable calcium phosphate compounds may be used in the respective first and second phases, and many of the heretofore discussed calcium compounds are deemed particularly suitable. Generally, it is preferred that the Ca/P ratio ranges from 0.5 to 2.0 in each phase. In some embodiments, particularly when it is desired to form hydroxyapatite, one of the phases includes a calcium phosphate in which the Ca/P ratio is less than 5/3, and the other includes a calcium phosphate compound in which the Ca/P ratio is greater than 5/3. The Ca/P ratio in hydroxyapatite is 5/3, and it is believed that providing calcium and phosphate in both greater and lesser amounts will drive formation of hydroxyapatite. It is not necessary to employ two such phases, especially if a setting accelerator is used (as described hereinbelow). In some embodiments, the Ca/P ratio in one of the pastes is equal to 5/3. In the formation of hydroxyapatite with the heretofore described calcium phosphate cements, the formation of hydroxyapatite can proceed slowly if the cement is initially formed at a pH above about 8, and if the selection of precursors for such a cement would provide a pH of 8 or above, use of a setting accelerator is preferred. In some embodiments, one may choose the overall Ca/P in order to cause formation of a different calcium phosphate in the resulting cement, such as DCPA (as set forth in Example 42 below) or DCPD.

These cement chemistries are not mutually exclusive, and it is thus contemplated that a cement precursor system may include materials that, when blended, form a cement that has attributes of two or more of the heretofore described cements.

The nature of the compounds and functional materials present in the cements is not limited to the heretofore described ingredients, but to the contrary any other suitable osteoconductive, bioactive, bioinert, or other functional materials may be used in conjunction with the invention. When used, these optional ingredients, may be present in any amounts suitable for their intended purposes. For instance, particularly in the case of the calcium phosphate cements, one or both cement precursor phases may include a setting accelerator, such as phosphoric acid, hydrochloric acid, sulfuric acid, oxalic acid, and salts thereof, and sodium phosphate, potassium phosphate, and sodium fluoride. In some embodiments, some of the calcium phosphate materials themselves may promote setting; for instance, MCPM and certain nano-sized calcium phosphate materials may promote setting of the cement. Any other suitable setting accelerator may be used in conjunction with the present invention. Setting accelerators are described in more detail in Chow et al., U.S. Patent Application Publication No. 20050074415, published Apr. 7, 2005.

In some embodiments, one of the cement precursors includes an osteoinductive protein, by which is contemplated any protein that is useful in assisting in or inducing bone formation. Osteoinductive proteins are deemed particularly suitable for use in conjunction with the carboxyl/calcium cement systems because, at least for many known osteoinductive proteins, such proteins may denature at an alkaline pH.

Another optional ingredient is a filler, such as a radio opaque filler. The radio opaque filler may, for instance, be a suitable bismuth, barium, or iodide compound, such as barium sulfate or bismuth hydroxide. Other suitable fillers include bioglass, silicas, alumina, biphasic calcium phosphate, calcium silicate, calcium sulfate, granular calcium phosphate ceramics, Portland cement, and the like.

A medicament, such as zinc, magnesium, or any other suitable medicament may be included in one or both of the phases of the cement precursors.

Either or both of the phases may include a material that is intended to affect the viscosity, cohesiveness, or injectability of the phases. Any suitable biocompatible ingredient, such as hydroxypropyl methyl cellulose (HPMC) or the like may be employed in conjunction therewith.

In some embodiments, a macropore forming material may be used. As disclosed, for instance, in prior U.S. Pat. Nos. 7,018,460 and 6,955,716, a macropore forming material, such as mannitol, is useful in forming a macropores, or pores having a size greater than 150 microns. Such pores are sometimes deemed desirable and that they create a structure that may be useful in promoting growth of soft tissue in or near the region of these cements.

Also as described in prior U.S. Pat. Nos. 7,018,460 and 6,955,716, in some embodiments, one or more strength-enhancing components, such as fibers, meshes, or the like, may be used. Such components may be resorbable or non-resorbable.

The following Examples are provided to illustrate the invention, but should not be construed as limiting the invention in scope. All of these Examples describe dual-phase cement precursor systems in which two liquid pastes were prepared, the pasted being denoted as Paste 1 and Paste 2. An asterisk symbol ("*") denotes that both pastes are aqueous, and the absence of an asterisk symbol denotes that one paste is aqueous and the other paste is non-aqueous.

EXAMPLES

Examples 1-25 describe carboxyl/calcium cement systems.

Example 1

Paste 1 was prepared by blending 3.0 g of barium sulfate ($BaSO_4$) and 0.12 g hydroxypropyl methyl cellulose (HPMC) into 1.5 mL of an aqueous solution (8.5 M) of glycolic acid. Paste 2 was composed of 3 g of a calcium phosphate cement (CPC) mixture (containing 73% tetracalcium phosphate (TTCP) and 27% dicalcium phosphate anhydrous (DCPA)) and 1.0 g of glycerin. Approximately equal volumes of the two pastes were dispensed and homogeneously mixed using a dual-barrel micro dispenser (1:1 volume ratio) equipped with a static mixer in the delivery tip. The combined pastes hardened in less than 5 minutes at room temperature (21° C.).

Both pastes were aged for ten days at 50° C. No measurable changes in paste consistency or setting reaction was observed. Diametral tensile strength (DTS) was evaluated under the methodology described in Lemaitre et al., "Setting, Hardening and Resorption of Calcium Phosphate Hydraulic Cements," *Rev Stomatol. Chir. Maxiffofac.* 1992; 93:163-165. The DTS of 1-day set cement sample was 2.52±0.37 MPa (n=5). Without limiting the scope of the claims of the invention, in general a DTS in the range of 1.2 MPA to 3.5 MPa is deemed satisfactory, and accordingly this cement was deemed to be satisfactory.

Example 1a

Paste 1 was prepared by blending 2.5 g of monocalcium phosphate monohydrate (MCPM) into 1.0 ml of an aqueous solution (8.5 M) of glycolic acid. Paste 2 was composed of 2.5 g of a calcium phosphate cement (CPC) mixture (containing 73% tetracalcium phosphate (TTCP) and 27 dicalcium phosphate anhydrous (DCPA)) and 1.0 g of polyethylene glycol 400. Approximately equal volumes of the two pastes were dispensed and homogeneously mixed using a dual-barrel micro dispenser (1:1 volume ratio) equipped with a static mixer in the delivery tip. The combined pastes hardened about 5 minutes at room temperature (21° C.). Diametral tensile strength (DTS) of 1-day set cement sample was 1.40±0.02 Pa (n=3).

Example 1B

Paste 1 was prepared by blending 2.54 g of monocalcium phosphate monohydrate (MCPM) into 1.0 ml of an aqueous solution (8.5 M) of glycolic acid. Paste 2 was composed of 2.5 g of a tetracalcium phosphate (TTCP) and 1.0 g of polyethylene glycol 400. Approximately equal volumes of the two pastes were dispensed and homogeneously mixed using a dual-barrel micro dispenser (1:1 volume ratio) equipped with a static mixer in the delivery tip. The combined pastes hardened about 5 minutes at room temperature (21° C.). Diametral tensile strength (DTS) of 1-day set cement sample was 1.84±0.08 MPa (n=4).

Example 2

Paste 1 was prepared by blending 3.0 g of barium sulfate into 1.5 mL of an aqueous solution (8.5 M) of tartaric acid. Paste 2 was composed of 3 g of a calcium phosphate cement (CPC) mixture (containing 73% tetracalcium phosphate (TTCP) and 27% dicalcium phosphate anhydrous (DCPA)) and 1.2 g of glycerin. Approximately equal volumes of the two pastes were dispensed and homogeneously mixed using a dual-barrel micro dispenser (1:1 volume ratio) equipped with a static mixer in the delivery tip. The combined pastes hardened in less than 5 minutes at room temperature (21° C.).

Example 3

Paste 1 was prepared by blending 3.0 g of alumina ($Al_2O_3$) into 1.5 mL of an aqueous solution (8.5 M) of glycolic acid. Paste 2 was composed of 3 g of a calcium phosphate cement (CPC) mixture (containing 73% tetracalcium phosphate (TTCP) and 27% dicalcium phosphate anhydrous (DCPA)) and 1.1 g of glycerin. Approximately equal volumes of the two pastes were dispensed and homogeneously mixed using a dual-barrel micro dispenser (1:1 volume ratio) equipped with a static mixer in the delivery tip. The combined pastes hardened in approximately 5 minutes at room temperature (21° C.).

Example 4

Paste 1 was composed of 3.0 g of TTCP and 1.3 mL of water. Paste 2 was composed of 3 g of glycolic acid granules and 1 g of glycerin. Approximately equal volumes of the two pastes were dispensed and homogeneously mixed using a dual-barrel micro dispenser (1:1 volume ratio) equipped with a static mixer in the delivery tip. The combined pastes hardened in 2-3 minutes at room temperature (21° C.).

Example 5

Paste 1 was composed of 3.0 g of TTCP and 1.3 mL of water. Paste 2 was composed of 3 g of maleic acid granules and 1 g of glycerin. Approximately equal volumes of the two pastes were dispensed and homogeneously mixed using a dual-barrel micro dispenser (1:1 volume ratio) equipped with a static mixer in the delivery tip. The combined pastes hardened almost instantly at room temperature (21° C.).

Example 6

Paste 1 was composed of 3.0 g of TTCP and 1.5 mL of water. Paste 2 was composed of 3 g of citric acid granules and 1 g of glycerin. Approximately equal volumes of the two pastes were dispensed and homogeneously mixed using a dual-barrel micro dispenser (1:1 volume ratio) equipped with a static mixer in the delivery tip. The combined pastes hardened in approximately 30 minutes at room temperature (21° C.).

Example 7

Paste 1 was composed of 4.0 g of monocalcium phosphate monohydrate (MCPM) and 1.5 mL of an aqueous solution (8.5 M) of glycolic acid. Paste 2 was composed of 1.5 g of calcium glycerophosphate, 1.5 g of calcium hydroxide, and 1 g of glycerin. Approximately equal volumes of the two pastes were dispensed and homogeneously mixed using a dual-barrel micro dispenser (1:1 volume ratio) equipped with a static mixer in the delivery tip. The combined pastes hardened instantly at room temperature (21° C.).

Example 8

Paste 1 was composed of 3.0 g of TTCP and 1.5 mL of water. Paste 2 was composed of 2 g of tartaric acid granules, 1 g MCPM and 1.5 g of glycerin. Approximately equal volumes of the two pastes were dispensed and homogeneously mixed using a dual-barrel micro dispenser (1:1 volume ratio) equipped with a static mixer in the delivery tip. The combined pastes hardened almost immediately at room temperature (21° C.).

Example 9*

Paste 1 was composed of 3.0 g of beta-tricalcium phosphate (β-TCP) and 1.3 mL of water. Paste 2 was composed of 3 g of $Al_2O_3$ and 1.5 mL of an aqueous solution (8.5 M) of glycolic acid. Approximately equal volumes of the two pastes were dispensed and homogeneously mixed using a dual-barrel micro dispenser (1:1 volume ratio) equipped with a static mixer in the delivery tip. The combined pastes hardened instantly at room temperature (21° C.).

Example 10

Paste 1 was composed of 3 g of $Al_2O_3$ and 1.5 mL of an aqueous solution (8.5 M) of glycolic acid. Paste 2 was composed of 3.0 g of alpha-tricalcium phosphate ($\alpha$-TCP) and 1.4 g polyethylene glycol 400. Approximately equal volumes of the two pastes were dispensed and homogeneously mixed using a dual-barrel micro dispenser (1:1 volume ratio) equipped with a static mixer in the delivery tip. The combined pastes hardened instantly at room temperature (21° C.).

Example 11*

Paste 1 was composed of 3.0 g of commercially obtained hydroxyapatite (HA) (bio-Rad) and 2.5 mL of water. Paste 2 was composed of 3 g of $Al_2O_3$ and 1.5 mL of an aqueous solution (8 M) of tartaric acid. Approximately equal volumes of the two pastes were dispensed and homogeneously mixed using a dual-barrel micro dispenser (1:1 volume ratio) equipped with a static mixer in the delivery tip. The combined pastes hardened in approximately 5 minutes at room temperature (21° C.).

Example 12

Paste 1 was composed of 3 g of $BaSO_4$ and 1.2 mL of an aqueous solution (8.5 M) of glycolic acid. Paste 2 was composed of 1.2 g of amorphous calcium phosphate (ACP) and 1.2 g glycerin. Approximately equal volumes of the two pastes were dispensed and homogeneously mixed using a dual-barrel micro dispenser (1:1 volume ratio) equipped with a static mixer in the delivery tip. The combined pastes hardened in 2 to 3 minutes at room temperature (21° C.).

Example 13

Paste 1 was composed of 3 g of $BaSO_4$ and 1.3 mL of an aqueous solution (8.5 M) of glycolic acid. Paste 2 was composed of 1.5 g of octacalcium phosphate (OCP) and 1.8 g glycerin. Approximately equal volumes of the two pastes were dispensed and homogeneously mixed using a dual-barrel micro dispenser (1:1 volume ratio) equipped with a static mixer in the delivery tip. The combined pastes hardened in less than 5 minutes at room temperature (21° C.).

Example 14

Paste 1 was composed of 3 g of $BaSO_4$ and 1.0 mL of an aqueous solution (14 M) of malonic acid. Paste 2 was composed of 2.9 g of a CPC mixture consisting of 3 moles of $\alpha$-TCP and 1 mole of $CaCO_3$ (Ca/P molar ratio=1.67) and 1.5 g glycerin. Approximately equal volumes of the two pastes were dispensed and homogeneously mixed using a dual-barrel micro dispenser (1:1 volume ratio) equipped with a static mixer in the delivery tip. The combined pastes hardened in approximately 50 minutes at room temperature (21° C.).

Example 15

Paste 1 was composed of 3.1 g of $BaSO_4$ and 1.2 mL of an aqueous solution (8.5 M) of glycolic acid. Paste 2 was composed of 1.6 g of a CPC mixture consisting of 3 moles of dicalcium phosphate anhydrous (DCPA) and 2 moles of $Ca(OH)_2$ (Ca/P molar ratio=1.67) and 1.4 g glycerin. Approximately equal volumes of the two pastes were dispensed and homogeneously mixed using a dual-barrel micro dispenser (1:1 volume ratio) equipped with a static mixer in the delivery tip. The combined pastes hardened in approximately 10 minutes at room temperature (21° C.).

Example 16

Paste 1 was composed of 3 g of $BaSO_4$ and 1.2 mL of an aqueous solution (8.5 M) of glycolic acid. Paste 2 was composed of 1.6 g of a CPC mixture consisting of 3 moles of DCPA and 2 moles of $Ca(OH)_2$ (Ca/P molar ratio=1.67) and 1.4 g glycerin. Approximately equal volumes of the two pastes were dispensed and homogeneously mixed using a dual-barrel micro dispenser (1:1 volume ratio) equipped with a static mixer in the delivery tip. The combined pastes hardened in approximately 10 minutes at room temperature (21° C.).

Example 17*

Paste 1 was composed of 1.5 g of MCPM, 1.5 g of DCPD, 1.7 g of glycolic acid granules, and 3 mL of a solution saturated with respect to both MCPM and DCPD ([Ca]=1.3 M, [P]=4.4 M, pH=1.9). Paste 2 was composed of 3 g of a TTCP and 1.3 mL of water. Approximately equal volumes of the two pastes were dispensed and homogeneously mixed using a dual-barrel micro dispenser (1:1 volume ratio) equipped with a static mixer in the delivery tip. The combined pastes set instantly at room temperature (21° C.).

Example 18*

Paste 1 was composed of 1.5 g of MCPM, 1.5 g of DCPD, 1.7 g of glycolic acid granules, and 3 mL of a solution saturated with respect to both MCPM and DCPD ([Ca]=1.3 M, [P]=4.4 M, pH=1.9). Paste 2 was composed of 3 g of a TTCP, 0.75 mL of water, and 0.75 g of glycerin. Approximately equal volumes of the two pastes were dispensed and homogeneously mixed using a dual-barrel micro dispenser (1:1 volume ratio) equipped with a static mixer in the delivery tip. The combined pastes set in less than 5 minutes at room temperature (21° C.).

Example 19*

Paste 1 was composed of 3 g of DCPA and 1.4 mL of an aqueous solution (2 M) of citric acid. Paste 2 was composed of 3 g of TTCP and 1.4 mL of water. Approximately equal volumes of the two pastes were dispensed and homogeneously mixed using a dual-barrel micro dispenser (1:1 volume ratio) equipped with a static mixer in the delivery tip. The combined pastes set almost immediately at room temperature (21° C.). Diametral tensile strength of 1-day set cement sample was 4.18±1.02 MPa (n=5).

Example 20

Paste 1 was composed of 3 g of DCPA and 1.4 mL of an aqueous solution (2 M) of citric acid. Paste 2 was composed of 3 g of TTCP and 1.35 g of glycerin. Approximately equal volumes of the two pastes were dispensed and homogeneously mixed using a dual-barrel micro dispenser (1:1 volume ratio) equipped with a static mixer in the delivery tip. The combined pastes set in less than 10 minutes at room tempera-

Example 21*

Paste 1 was composed of 3 g of DCPA and 1.4 mL of an aqueous solution (2 M) of citric acid. Paste 2 was composed of 3 g of TTCP, 0.5 g of water and 1 g of glycerin. Approximately equal volumes of the two pastes were dispensed and homogeneously mixed using a dual-barrel micro dispenser (1:1 volume ratio) equipped with a static mixer in the delivery tip. The combined pastes set in less than 5 minutes at room temperature (21° C.).

Example 22

Paste 1 was composed of 3 g of $Ca(OH)_2$ and 2 mL of water. Paste 2 was composed of 3 g of citric acid granules and 1 g of glycerin. Approximately equal volumes of the two pastes were dispensed and homogeneously mixed using a dual-barrel micro dispenser (1:1 volume ratio) equipped with a static mixer in the delivery tip. The combined pastes set in less than 5 minutes at room temperature (21° C.).

Example 23*

Paste 1 was composed of 1.5 g of ground DCPA, 0.01 g of HPMC and 1.2 g of an aqueous solution (2M) of malic acid solution. Paste 2 was composed of 1.5 g of TTCP and 0.7 g of 1% HPMC aqueous solution. Approximately equal volumes of the two pastes were dispensed and homogeneously mixed using a dual-barrel micro dispenser (1:1 volume ratio) equipped with a static mixer in the delivery tip. The combined pastes set in less than 5 minutes at room temperature (21° C.). Diametral tensile strength (DTS) of 1-day set cement sample was 3.48±0.40 MPa (n=5).

Example 24

Paste 1 was composed of 2 g of MCPM, 1 g of an aqueous solution (8.5 M) of glycolic acid solution and 0.1 g of glycerin. Paste 2 was composed of 3 g of Portland cement and 1.2 g of glycerin. Approximately equal volumes of the two pastes were dispensed and homogeneously mixed using a dual-barrel micro dispenser (1:1 volume ratio) equipped with a static mixer in the delivery tip. The combined pastes set in about 9 minutes at room temperature (21° C.). Diametral tensile strength of 1-day set cement sample was 2.31±0.65 MPa (n=5).

Example 25

Paste 1 was composed of 3 g of MCPM, 1.25 g of an aqueous solution (8.5M) of glycolic acid solution. Paste 2 was composed of 3 g of tricalcium silicate and 2 g of glycerin. Approximately equal volumes of the two pastes were dispensed and homogeneously mixed using a dual-barrel micro dispenser (1:1 volume ratio) equipped with a static mixer in the delivery tip. The combined pastes set in about 4 minutes at room temperature (21° C.).

Examples 26-35 describe hydrogel cement systems

Example 26

Paste 1 was prepared by blending 3.0 g of MCPM into 2.5 g of a chitosan lactate solution (15% chitosan lactate+85% water). Paste 2 was composed of 3 g of a calcium phosphate cement (CPC) mixture (containing 73% tetracalcium phosphate (TTCP) and 27% dicalcium phosphate anhydrous (DCPA)) and 1.2 g of glycerin. Approximately equal volumes of the two pastes were dispensed and homogeneously mixed using a dual-barrel micro dispenser (1:1 volume ratio) equipped with a static mixer in the delivery tip. The combined pastes set in approximately 5 minutes at room temperature (21° C.) forming a non-rigid hard mass. Diametral tensile strength of 1-day set cement sample was 2.15±0.21 MPa (n=5).

Example 27*

Paste 1 was prepared by blending 3.0 g of $BaSO_4$ into 1.5 g of a sodium alginate solution (20% sodium alginate+80% water). Paste 2 was composed of 3 g of a DCPA and 1.5 mL of a pH 2.1 solution saturated with respect to dicalcium phosphate dihydrate. Approximately equal volumes of the two pastes were dispensed and homogeneously mixed using a dual-barrel micro dispenser (1:1 volume ratio) equipped with a static mixer in the delivery tip. The combined pastes set in approximately 5 minutes at room temperature (21° C.).

Example 28

Paste 1 was composed of 2.5 g of MCPM, 1.8 g of a chitosan lactate solution (15% chitosan lactate+85% water), and 1 g of glycerin. Paste 2 was composed of 3 g of calcium carbonate and 1 g of glycerin. Approximately equal volumes of the two pastes were dispensed and homogeneously mixed using a dual-barrel micro dispenser (1:1 volume ratio) equipped with a static mixer in the delivery tip. The combined pastes set in approximately 5 minutes at room temperature (21° C.) forming a non-rigid hard mass.

Example 29

Paste 1 was composed of 2.5 g of MCPM, 1.8 g of a chitosan lactate solution (15% chitosan lactate+85% water), and 1 g of glycerin. Paste 2 was composed of 3 g of a calcium phosphate cement (CPC) mixture (containing 73% tetracalcium phosphate (TTCP) and 27% dicalcium phosphate anhydrous (DCPA)) and 1.5 g of glycerin. Approximately equal volumes of the two pastes were dispensed and homogeneously mixed using a dual-barrel micro dispenser (1:1 volume ratio) equipped with a static mixer in the delivery tip. The combined pastes set almost immediately at room temperature (21° C.) forming a non-rigid hard mass.

Example 30

Paste 1 was composed of 3 g of TTCP and 1.4 mL of water. Paste 2 was composed of 2 g of chitosan malate and 1 g of glycerin. Approximately equal volumes of the two pastes were dispensed and homogeneously mixed using a dual-barrel micro dispenser (1:1 volume ratio) equipped with a static mixer in the delivery tip. The combined pastes set almost instantly at room temperature (21° C.) forming a non-rigid hard mass.

Example 31

Paste 1 was composed of 3 g of $CaCO_3$ and 1.5 mL of water. Paste 2 was composed of 2 g of chitosan malate and 1 g of glycerin. Approximately equal volumes of the two pastes were dispensed and homogeneously mixed using a dual-barrel micro dispenser (1:1 volume ratio) equipped with a static mixer in the delivery tip. The combined pastes set in approximately 5 minutes at room temperature (21° C.) forming a non-rigid hard mass.

Example 32

Paste 1 was prepared by blending 3 g of MCPM into 3 g of a chitosan lactate solution (15% chitosan lactate+85% water). Paste 2 was composed of 3 g of a Portland cement and 1.2 g of glycerin. Approximately equal volumes of the two pastes were dispensed and homogeneously mixed using a dual-barrel micro dispenser (1:1 volume ratio) equipped with a static mixer in the delivery tip. The combined pastes set in approximately 1 minutes at room temperature (21° C.) forming a non-rigid hard mass. Diametral tensile strength (DTS) of 1-day set cement sample was 2.26±0.75 MPa (n=5).

Example 33

Paste 1 was prepared by blending 1 g of DCPA and 1.2 g of barium sulfate into 1.1 g of a chitosan lactate solution (15% chitosan lactate+85% water). Paste 2 was composed of 1.4 g of TTCP, 0.6 g of tricalcium silicate, 0.2 g of $Na_2HPO_4$, and 1.2 g of glycerin. Approximately equal volumes of the two pastes were dispensed and homogeneously mixed using a dual-barrel micro dispenser (1:1 volume ratio) equipped with a static mixer in the delivery tip. The combined pastes set in approximately 10 minutes at room temperature (21° C.) forming a non-rigid hard mass. Diametral tensile strength of 1-day set cement sample was 2.06±0.37 MPa (n=5).

Example 34

Paste 1 was prepared by blending 2 g of DCPA and 1 g of MCPM into 1.5 g of a chitosan lactate solution (5% chitosan lactate+95% water). Paste 2 was composed of 3 g of TTCP and 1.7 g of glycerin. Approximately equal volumes of the two pastes were dispensed and homogeneously mixed using a dual-barrel micro dispenser (1:1 volume ratio) equipped with a static mixer in the delivery tip. The combined pastes set in approximately 20 minutes at room temperature (21° C.) forming a non-rigid hard mass.

Example 35

Paste 1 was prepared by blending 3.0 g of TTCP into 1.5 g of a sodium alginate solution (20% sodium alginate+80% water), and 0.1 g of glycerin. Paste 2 was composed of 3 g of a DCPA and 1.5 mL of a pH 2.1 solution saturated with respect to dicalcium phosphate dihydrate. Approximately equal volumes of the two pastes were dispensed and homogeneously mixed using a dual-barrel micro dispenser (1:1 volume ratio) equipped with a static mixer in the delivery tip. The combined pastes set in approximately 20 minutes at room temperature (21° C.) forming a non-rigid hard mass.

Example 36-39 describe cement systems in which both carboxyl/calcium cements and hydrogel cements are employed.

Example 36

Paste 1 was prepared by combining 3.0 g of barium sulfate ($BaSO_4$), 0.18 g of chitosan lactate, and 1.8 g of an aqueous solution (8.5M) of glycolic acid. Paste 2 was composed of 3 g of TTCP and 1.3 mL of water. Approximately equal volumes of the two pastes were dispensed and homogeneously mixed using a dual-barrel micro dispenser (1:1 volume ratio) equipped with a static mixer in the delivery tip. The combined pastes hardened almost immediately.

Example 37

Paste 1 was prepared by blending 3 g of MCPM into 4 g of an aqueous solution containing 8.5 M glycolic acid and 10 wt % chitosan lactate. Paste 2 was composed of 3 g Portland cement and 1.2 g of glycerin. Approximately equal volumes of the two pastes were dispensed and homogeneously mixed using a dual-barrel micro dispenser (1:1 volume ratio) equipped with a static mixer in the delivery tip. The combined pastes hardened in 5 minutes at 37° C. Diametral tensile strength (DTS) of 1-day set cement sample was 2.05±0.32 MPa (n=5).

Example 38

Paste 1 was prepared by blending 3 g of MCPM into 4 g of an aqueous solution containing 8.5 M glycolic acid and 10 wt % chitosan lactate. Paste 2 was composed of 3 g TTCP, 0.015 g HPMC, and 1.5 g of glycerin. Approximately equal volumes of the two pastes were dispensed and homogeneously mixed using a dual-barrel micro dispenser (1:1 volume ratio) equipped with a static mixer in the delivery tip. The combined pastes hardened less than 5 minutes at 37° C.

Example 39

Paste 1 was prepared by blending 3 g of MCPM into 4 g of an aqueous solution containing 8.5M glycolic acid and 10 wt % chitosan lactate. Paste 2 was composed of 3 g of a calcium phosphate cement (CPC) mixture (containing 73 wt % TTCP and 27 wt % DCPA) and 1.2 g of glycerin. Approximately equal volumes of the two pastes were dispensed and homogeneously mixed using a dual-barrel micro dispenser (1:1 volume ratio) equipped with a static mixer in the delivery tip. The combined pastes hardened less than 5 minutes at 37° C.

Examples 40-42 and 43-45 describe calcium phosphate cement systems.

Example 40

Paste 1 was composed of 3.0 g of MCPM, 0.1 g of hydroxypropyl methyl cellulose (HPMC) and 1.5 mL of a solution saturated with respect to both MCPM and DCPD ([Ca]=1.3M, [P]=4.4 M, pH=1.9). Paste 2 was composed of 3 g of a TTCP and 2 g of glycerin. Approximately equal volumes of the two pastes were dispensed and homogeneously mixed using a dual-barrel micro dispenser (1:1 volume ratio) equipped with a static mixer in the delivery tip. The combined pastes set almost instantly at room temperature (21° C.).

Example 41

Paste 1 was composed of 3 g of DCPA, 0.1 g of hydroxypropyl methyl cellulose (HPMC) and 2 mL of a 1 M $NaH_2PO_4$ solution. Paste 2 was composed of 3 g of a TTCP and 2 g of glycerin. Approximately equal volumes of the two pastes were dispensed and homogeneously mixed using a dual-barrel micro dispenser (1:1 volume ratio) equipped with a static mixer in the delivery tip. The combined pastes set in approximately 5 minutes at room temperature (21° C.).

Example 42

Paste 1 was composed of 3.0 g of MCPM, 0.017 g of hydroxypropyl methyl cellulose (HPMC), 1.5 g of a solution saturated with respect to both MCPM and DCPD ([Ca]=1.3 M, [P]=4.4 M, pH=1.9), and 0.5 g of glycerin. Paste 2 was composed of 3 g of a calcium phosphate cement (CPC) mixture (containing 73 wt % TTCP and 27 wt % DCPA), 0.017 g of HPMC, and 1.2 g of glycerin.

Approximately equal volumes of the two pastes were dispensed and homogeneously mixed using a dual-barrel micro dispenser (1:1 volume ratio) equipped with a static mixer in the delivery tip. The combined pastes hardened less than 10 minutes at 37° C. Diametral tensile strength of 1-day set cement sample was 2.39±0.60 MPa (n=5).

Comparative Example 1

A dual-paste cement identical to the one given in Example 2 of U.S. Patent Application 20040244651 (Lemaitre et al, 2004) was prepared. Paste 1 was composed of 1.36 g of DCPA, 2.3 g of HA ($Ca_5(PO_4)_3OH$), and 1.85 g of 10 mmol/l of orthophosphoric acid. Paste 2 of the cement was composed of 3.66 g of TTCP and 1.85 g of sterile water. Approximately equal volumes of the two pastes were dispensed and homogeneously mixed using a dual-barrel micro dispenser (1:1 volume ratio) equipped with a static mixer in the delivery tip. The combined pastes did not set within 60 minutes at 37° C. Because this cement hardened too slowly, another dual paste cement that additionally contained a setting accelerator was described next.

Comparative Example 2

A dual-paste cement similar to the one given in Example 2 of U.S. Patent Application 20040244651 (Lemaitre et al, 2004) was prepared. Paste 1 was composed of 1.36 g of DCPA, 2.3 g of HA ($Ca_5(PO_4)_3OH$), and 1.15 g of an aqueous solution (1.5 M) of $NaH_2PO_4$, a setting accelerator. Paste 2 of the cement was composed of 3.66 g of TTCP and 1.85 g of sterile water. Approximately equal volumes of the two pastes were dispensed and homogeneously mixed using a dual-barrel micro dispenser (1:1 volume ratio) equipped with a static mixer in the delivery tip. The combined pastes set in approximately 25 minutes at 37° C.

The two cement pastes, kept in separate air tight containers, were aged for 7 days at 50° C. The setting time of cement samples prepared from the aged pastes was greater than 4 days. This result indicates that one or both of the cement pastes had lost reactivity as a result of aging.

Example 43

A dual-paste cement similar to that prepared in Comparative Example 2 was prepared, except that paste 2 was water-free. Paste 1 was composed of 1.36 g of DCPA, 2.3 g of HA ($Ca_5(PO_4)_3OH$), and 1.15 g of an aqueous solution (1.5 M) of $NaH_2PO_4$. Paste 2 of the cement was composed of 3.66 g of TTCP and 2.28 g of glycerin. Approximately equal volumes of the two pastes were dispensed and homogeneously mixed using a dual-barrel micro dispenser (1:1 volume ratio) equipped with a static mixer in the delivery tip. The combined pastes set in approximately 25 minutes at 37° C.

The two cement pastes, kept in separate air tight containers, were aged for 7 days at 50° C. The setting time of cement samples prepared from the aged pastes was about 22 minutes. This result indicates that neither cement paste had lost reactivity as a result of aging. By removing water from the second paste, it was seen that the stability of the system was enhanced significantly.

Example 44

Paste 1 was composed of 3.0 g of MCPM, 0.017 g of hydroxypropyl methyl cellulose (HPMC), 1.5 g of a solution saturated with respect to both MCPM and DCPD ([Ca]=1.3 M, [P]=4.4 M, pH=1.9). Paste 2 was composed of 3 g of a α-tricalcium phosphate, 0.017 g of HPMC, 0.018 g of HPMC, and 1.74 g of glycerin. Approximately equal volume of the two pastes were dispensed and homogeneously mixed using a dual-barrel micro dispenser (1:1 volume ratio) equipped with a static mixer in the delivery tip. The combined pastes hardened less than 7 minutes at 37° C. Diametral tensile strength of 1-day set cement sample was 1.31±0.26 MPa (n=3).

Example 45

Paste 1 was composed of 3.0 g of MCPM, 0.017 g of hydroxypropyl methyl cellulose (HPMC), 1.5 g of a solution saturated with respect to both MCPM and DCPD ([Ca]=1.3 M, [P]=4.4 M, pH=1.9). Paste 2 was composed of 3 g of a β-tricalcium phosphate, 0.017 g of HPMC, 0.018 g of HPMC, and 1.74 g of glycerin. Approximately equal volume of the two pastes were dispensed and homogeneously mixed using a dual-barrel micro dispenser (1:1 volume ratio) equipped with a static mixer in the delivery tip. The combined pastes hardened less than 7 minutes at 37° C. Diametral tensile strength of 1-day set cement sample was 2.28±0.27 MPa (n=5).

It is thus seen that the present invention provides, in various preferred embodiments, dual-phase cement precursor systems, and related kits and methods. The cements of the invention are bio-compatible, in that they are compatible with soft and hard tissues. In preferred embodiments, the cements are osteoconductive and do not cause chronic inflammation of tissues. The cements preferably are injectable, and, when injected, blending is caused during injection, thus permitting the surgeon the maximum amount of time between injection of the cement and hardening of the cement. Through modification of the various cement chemistries employed in connection with the present invention, a range of hardening times, a range of physical and strength properties, and a range of in vivo absorption rates may be realized.

All references, including publications, patent applications, and patents, cited herein are hereby incorporated by reference. In any listing of possible ingredients or components, mixtures of the possible ingredients or components are contemplated unless expressly indicated otherwise. The description of certain embodiments as "preferred" embodiments, and other recitation of embodiments, features, or ranges as being preferred, is not deemed to be limiting, and the invention is deemed to encompass embodiments that are presently deemed to be less preferred. All methods described herein can be performed in any suitable order unless otherwise indicated herein or otherwise clearly contradicted by context. The use of any and all examples, or exemplary language (e.g., "such as") provided herein, is intended to illuminate the invention and does not pose a limitation on the scope of the invention unless otherwise claimed. Any statement herein as to the nature or benefits of the invention or of the preferred embodiments is not intended to be limiting, and the appended claims should not be deemed to be limited by such statements. For instance, the heretofore described parameters for evaluating the stability of a precursor phase are not deemed to be limiting, unless otherwise specified in the claims. More generally, no language in the specification should be construed as indicating any non-claimed element as being essential to the practice of the invention. This invention includes all modifications and equivalents of the subject matter recited in the claims appended hereto as permitted by applicable law. Moreover, any combination of the above-described elements in all possible variations thereof is encompassed by the invention unless otherwise indicated herein or otherwise clearly contradicted by context. The description herein of any reference or patent as "prior" is not intended to constitute a concession that such reference is available as prior art against the present invention.

What is claimed:

1. A dual-phase bone and dental repair biocompatible, bioresorbable, calcium phosphate cement precursor system, said system comprising at least a first discrete aqueous phase and a second discrete nonaqueous phase which in combination are capable of reacting to form a cement with a setting time of between about 1 minute and 20 minutes and the phases have a shelf life of 7 days or more, said first phase consisting essentially of one or more first calcium compounds and further consisting of one or more carboxyl compounds selected from the group consisting of a carboxylic acid and a carboxylate, said second phase consisting essentially of one or more second calcium compounds which are all different from the first phase calcium compounds, at least one of said first and second phase calcium compounds consisting of a phosphate compound, said first and second phases being unmixed, and said first and second phases in combination characterized as cement precursors by reaction between said first phase compounds and second phase compounds to form said biocompatible, bioactive, bioresorbable cement upon mixing, each of said discrete first and second phases consisting essentially of a stable, non-hardenable paste prior to mixing, said first phase having a pH sufficiently acidic to preclude dissociation of said carboxyl compounds prior to mixing with said second phase.

2. A dual-phase cement precursor system according to claim 1 wherein at least one of said first phase and said second phase is in combination with one or more additional selected materials from the group consisting of an osteoinductive agent, a radio opaque filler, a macro forming agent, a medicament, a viscosity enhancing agent, and a strength enhancing agent.

3. A dual-phase cement precursor system according to claim 1, wherein said carboxyl compound comprises at least one acid or salt selected from the group consisting of glycolic, citric, tartaric, glycerophosphoric, malonic, malic, and maleic acids and salts.

4. A dual-phase cement precursor system according to claim 1, said one of said first and second phase calcium compounds being selected from the group consisting of monocalcium phosphate anhydrous, monocalcium phosphate monohydrate, dicalcium phosphate anhydrous, dicalcium phosphate dihydrate, octacalcium phosphate, alpha-tricalcium phosphate, beta-tricalcium phosphate, amorphous calcium phosphate, calcium hydroxyapatite, calcium deficient hydroxyapatite, carbonate-containing hydroxyapatite, and fluoride-containing hydroxyapatite.

5. A dual phase cement precursor system according to claim 1 wherein said first phase and said second phase have an approximately equal volume ratio prior to mixing.

6. A dual phase cement precursor system as set forth in claim 5 wherein said one or more first phase calcium compounds comprise dicalcium phosphate anhydrous and said one or more second phase calcium compounds comprise tetracalcium phosphate.

7. A dual-phase cement precursor system as set forth in claim 1 wherein, said one or more first phase calcium compounds comprise a first calcium phosphate compound.

8. A dual phase cement precursor system as set forth in claim 1 wherein said one or more first phase calcium compounds comprise a dicalcium phosphate anhydrous compound.

9. A dual phase cement precursor system as set forth in claim 1 wherein said one or more second phase calcium compounds comprise a calcium phosphate compound.

10. A dual phase cement precursor system as set forth in claim 1 wherein said one or more second phase calcium compounds comprise tetracalcium phosphate.

11. A dual phase cement precursor system as set forth in claim 1 wherein said one or more first phase calcium compounds comprise dicalcium phosphate anhydrous and said one or more second phase calcium compounds comprise tetracalcium phosphate.

12. A dual phase cement precursor system as set forth in claim 1 wherein the first calcium compound is selected from the group consisting of MCPM, DCPA and combinations thereof.

13. A dual phase cement precursor system as set forth in claim 1 wherein the aqueous phase includes a calcium phosphate compound and has a molar Ca/P ratio in the range of 0.5 to 2.0.

14. The dual phase cement precursor system of claim 13, wherein the molar Ca/P ratio in the range of 0.5 to 1.0.

15. A dual phase cement precursor system as set forth in claim 1 wherein the phases are mixed to form a cement and wherein the volumetric ratio of the mixed phases is in the range of about 0.1 to 10.

16. A dual phase cement precursor system as set forth in claim 15 wherein the volumetric ratio of the mixed phases is in the range of about 0.25 to 4.

17. A dual phase cement precursor system as set forth in claim 1 characterized by forming a hardened cement upon mixing said paste phase following storage of the unmixed paste phases for at least about seven days at 50° C.

18. A dual phase cement precursor system as set forth in claim 1 characterized by forming a hardened cement in less than about ten minutes upon mixing said separate phases following storage of the unmixed paste phases for at least about seven days at 50° C.

19. A dual phase cement precursor system as set forth in claim 1 characterized that each of the separate phases comprises a powder and a liquid in a powder/liquid (P/L) mass ratio of about 1/1 to 5/1.

20. The dual phase cement precursor system of claim 19, wherein the P/L mass ratio is about 2/1 to 4/1.

21. The dual phase cement precursor system of claim 1, wherein the setting time is between about 2 minutes and 10 minutes.

* * * * *

UNITED STATES PATENT AND TRADEMARK OFFICE
CERTIFICATE OF CORRECTION

Page 1 of 1

PATENT NO. : 9,259,439 B2
APPLICATION NO. : 11/550586
DATED : February 16, 2016
INVENTOR(S) : Laurence C. Chow et al.

It is certified that error appears in the above-identified patent and that said Letters Patent is hereby corrected as shown below:

In the Specification

The following should replace the paragraph at Column 1, Lines 20 - 24:
This invention was made with government support under grant R01 DE011789 awarded by the National Institutes of Health. The government has certain rights in the invention.

Signed and Sealed this
Thirteenth Day of July, 2021

Drew Hirshfeld
*Performing the Functions and Duties of the*
*Under Secretary of Commerce for Intellectual Property and*
*Director of the United States Patent and Trademark Office*